United States Patent [19]
Allen et al.

[11] Patent Number: 5,647,864
[45] Date of Patent: Jul. 15, 1997

[54] NONWOVEN FEMALE COMPONENT FOR REFASTENABLE FASTENING DEVICE AND METHOD OF MAKING THE SAME

[75] Inventors: Patrick Jay Allen; Beverly Jean Bross-Kelly, both of Cincinnati; Louis John Viltro, Hamilton; William Robert Vinnage, Jr.; David Michael Weirich, both of Cincinnati, all of Ohio

[73] Assignee: The Procter & Gamble Company, Cincinnati, Ohio

[21] Appl. No.: 547,847

[22] Filed: Oct. 25, 1995

Related U.S. Application Data

[63] Continuation of Ser. No. 254,814, Jun. 6, 1994, abandoned.

[51] Int. Cl.$^6$ .............................. A61F 13/15; A44B 1/04
[52] U.S. Cl. .............................. 604/391; 24/442; 24/448
[58] Field of Search .............................. 604/391; 24/442, 24/443, 444, 445, 446, 447, 448, 449, 450, 451, 452

[56] References Cited

U.S. PATENT DOCUMENTS

| | | |
|---|---|---|
| 2,039,312 | 5/1936 | Goldman . |
| 2,397,838 | 4/1946 | Chavannes . |
| 3,094,330 | 6/1963 | Smith . |
| 3,176,364 | 4/1965 | Dritz . |
| 3,206,343 | 9/1965 | McFarlane .............................. 156/72 |
| 3,214,323 | 10/1965 | Russell et al. . |
| 3,266,841 | 8/1966 | Altman . |
| 3,277,547 | 10/1966 | Billarant . |
| 3,319,307 | 5/1967 | Marforio . |
| 3,327,708 | 6/1967 | Sokolowski . |
| 3,405,430 | 10/1968 | Sidelman . |
| 3,469,289 | 9/1969 | Whitacre . |
| 3,490,107 | 1/1970 | Brumlik . |
| 3,494,006 | 2/1970 | Brumlik . |
| 3,527,629 | 9/1970 | Wylde .............................. 156/72 |
| 3,665,921 | 5/1972 | Stumpf . |
| 3,665,922 | 5/1972 | Skora . |
| 3,694,867 | 10/1972 | Stumpf . |
| 3,708,833 | 1/1973 | Ribich et al. . |
| 3,895,797 | 7/1975 | Moore . |
| 3,949,128 | 4/1976 | Ostermeier . |
| 4,116,892 | 9/1978 | Schwarz . |
| 4,169,303 | 10/1979 | Lemelson .............................. 24/204 |
| 4,223,059 | 9/1980 | Schwarz . |
| 4,355,066 | 10/1982 | Newman . |
| 4,374,888 | 2/1983 | Bornslaeger . |

(List continued on next page.)

FOREIGN PATENT DOCUMENTS

| | | |
|---|---|---|
| 0217032A3 | 4/1987 | European Pat. Off. . |
| 0258015 | 3/1988 | European Pat. Off. . |
| 0341993 | 11/1989 | European Pat. Off. . |
| 0604731A1 | 7/1994 | European Pat. Off. . |
| 0672516A2 | 9/1995 | European Pat. Off. . |
| 1140576 | 1/1969 | United Kingdom . |
| 1299897 | 12/1972 | United Kingdom . |
| WO92/01401 | 2/1992 | WIPO . |
| WO94/08789 | 4/1994 | WIPO . |
| WO95/04654 | 2/1995 | WIPO . |

*Primary Examiner*—Mary Beth Jones
*Attorney, Agent, or Firm*—David M. Weirich; Steven W. Miller; Jacobus C. Rasser

[57] ABSTRACT

A female component for a refastenable fastening device having an elastomeric adhesive backing and a multiplicity of fibrous elements extending from the backing. The female fastening component is formed by a method comprising the steps of: providing a first lamina comprising an elastomeric, pressure-sensitive adhesive film having a first adhesive surface and a second adhesive surface opposed to said first adhesive surface, a relaxed orientation and an elongated orientation; stretching said first lamina from said relaxed orientation to said elongated orientation; contacting a second lamina comprising a nonwoven web with said first surface of said first lamina in said elongated orientation, thereby directly joining said second lamina and said first lamina to form a laminate; and relaxing said first lamina such that said second lamina is shirred to form catching regions capable of entangling the hooks of a complementary male fastening component.

7 Claims, 7 Drawing Sheets

U.S. PATENT DOCUMENTS

| | | | |
|---|---|---|---|
| 4,379,192 | 4/1983 | Wahlquist et al. . | |
| 4,418,123 | 11/1983 | Bunnelle et al. | 428/517 |
| 4,600,618 | 7/1986 | Raychok, Jr. et al. . | |
| 4,725,473 | 2/1988 | Van Gompel et al. . | |
| 4,761,318 | 8/1988 | Ott et al. . | |
| 4,761,322 | 8/1988 | Raley . | |
| 4,789,699 | 12/1988 | Kieffer et al. | 524/271 |
| 4,891,258 | 1/1990 | Fahrenkrug | 428/138 |
| 4,923,456 | 5/1990 | Proxmire | 604/391 |
| 4,973,326 | 11/1990 | Wood et al. . | |
| 5,032,122 | 7/1991 | Noel et al. | 604/391 |
| 5,043,036 | 8/1991 | Swenson | 156/160 |
| 5,185,052 | 2/1993 | Chappell et al. | 156/462 |
| 5,308,345 | 5/1994 | Herrin . | |
| 5,326,612 | 7/1994 | Goulait | 428/100 |
| 5,354,591 | 10/1994 | Ott et al. | 428/99 |
| 5,447,590 | 9/1995 | Gilpatrick | 156/178 |
| 5,451,219 | 9/1995 | Suzuki et al. | 604/385.2 |

NONWOVEN FEMALE COMPONENT FOR REFASTENABLE FASTENING DEVICE AND METHOD OF MAKING THE SAME

This is a continuation of application Ser. No. 08/254,814, filed on Jun. 6, 1994, now abandoned.

FIELD OF THE INVENTION

The present invention relates to a female component for refastenable hook and loop type fastening devices and, more particularly, to a low-cost female component for a hook and loop type fastening device and a method for producing such a female fastening component.

BACKGROUND OF THE INVENTION

Refastenable fastening devices of the hook and loop type are currently used widely in a great number of situations. Such refastenable fastening devices have been particularly useful in clothing, disposable absorbent articles, and the like. Such devices are used when it is desirable to create a refastenable bond between two or more articles or between several surfaces of the same article. In certain applications, these refastenable fastening devices have replaced conventional buckles, zippers, buttons, snaps, tie fasteners, and sewing.

A popular type of mechanical fastener currently in wide use which utilizes mechanical entanglement to create a refastenable bond is sold under the trademark "VELCRO". VELCRO fastening devices are described in greater detail in U.S. Pat. No. 2,717,437, U.S. Pat. No. 3,009,235, U.S. Pat. No. 3,266,113, U.S. Pat. No. 3,550,837, U.S. Pat. No. 4,169,303, and U.S. Pat. No. 4,984,339.

VELCRO fasteners utilize two components. A male component and a female component. The male and female components are often referred to as the hook and loop components, respectively. The male component contains a plurality of resilient, upstanding hook shaped elements. The female component of the fastening device generally consists of a fabric containing a plurality of upstanding loops on its surface. When the male component and the loop component are pressed together in a face to face relationship to close the fastening device, the hooks entangle the loops forming a plurality of mechanical bonds between the individual hooks and loops. When these bonds have been created, the components will not generally disengage under normal conditions. This is because it is very difficult to separate the components by attempting to disengage all the hooks at once. However, when a gradual peeling force is applied to the components, disengagement can be easily effected. Under a peeling force, since the hooks are comprised of a resilient material, they will readily open to release the loops.

This type of fastening device has been found especially useful on disposable articles such as disposable garments, disposable diapers, disposable packages, cartons, and the like. Such fastening devices provide a secure closing means. However, the use of existing fastening devices of this type on disposable articles has been limited due to the fact that such fastening devices are relatively costly. A major reason that such fastening devices are costly is that they have high manufacturing costs. These high manufacturing costs are associated with both the hook and loop components of these devices.

Conventional hook and loop components are typically formed by making a fabric with a number of woven loops extending outwardly from a backing. The loops may be provided by weaving a base fabric containing supplementary threads to form the loops, or by knitting the loops into a fabric. In other hook and loop components, the loops may be formed by pleating or corrugating processes. The male components of such fastening devices are typically formed by subsequently cutting the loops. The cut loops serve as the hooks of the male component.

These processes generally produce costly hook and loop fastening materials because they are relatively slow. The hook and loop components of such fastening devices are also usually made out of the same relatively expensive material. This material is relatively expensive because the material used in the male component needs to be resilient so that the hooks can disengage from the loop component when the device is open.

Several attempts have been made to make alternative types of female components for fastening devices. However, such attempts have generally suffered from a number of drawbacks.

U.S. Pat. No. 3,694,867 issued to Stumpf on Oct. 3, 1972, discloses a "separable clasp" having a female component that comprises a "high loft" nonwoven fabric and a backing layer of consolidated flexible adhesive. However, the loop component disclosed in the Stumpf patent is prepared by performing the steps of: (1) activating an open pattern adhesive in which the fibers are imbedded, (2) consolidating the adhesive into a substantially continuous backing layer, and (3) simultaneously looping portions of the fibers such that the fibers form individual loops that extend outwardly from the backing. The female component disclosed in this patent suffers from the drawback that it is made by processes that involves mechanically manipulating fibers in the form of loops. Thus, the female components described therein do not appear to be significantly less expensive to manufacture than conventional loop components.

U.S. Pat. No. 4,761,318 issued to Ott, et al. on Aug. 2, 1988, discloses a loop fastener that can contemporaneously be both formed and also attached to a substrate without the need for any additional steps such as sewing or utilizing pressure sensitive adhesives to affix it to the substrate. However, the Ott loop fastener comprises a fibrous structure having a multiplicity of loops that is adhered to a layer of thermoplastic resin. Thus, the process disclosed in this patent suffers from the drawback that heat must be applied to bond the fibrous structure to the backing.

U.S. Pat. No. 3,708,833 issued to Ribich, et al. on Jan. 9, 1973, discloses a refastenable fastening device having a female component that comprises reticulated urethane foam secured to a backing layer. The female component disclosed in the Ribich, et al. patent suffers from the drawback that foams typically do not have enough openings for the hooks of conventional male components to penetrate. In addition, reticulated foam generally does not have sufficient strength to hold such hooks when forces are applied to the fastening device. Further, manufacturing reticulated foam is a relatively expensive process.

U.S. Pat. No. 5,032,122 issued to Noel, et al. on Jul. 16, 1991, discloses a loop fastening material having a backing of orientable material and a multiplicity of fibrous elements extending from the backing. The fibers are secured to the backing while the backing is in a dimensionally unstable state. The backing is then caused to be transformed to its dimensionally stable state thereby shearing the fibrous elements to form the catching regions of the loop material. Although the Noel patent discloses an acceptable low cost loop fastening material, the search has continued for more economical loop fastening materials and methods for producing such materials.

Thus, it is an object of the present invention to provide an improved fastening device for disposable articles.

It is another object of the present invention to provide an improved female component of a refastenable hook and loop type fastening device.

It is a further object of the present invention to provide a female component for a hook and loop type fastening device which may be formed by positioning a plurality of filaments on an elastomeric adhesive backing without manipulating the fibers into the form of loops to form a low cost loop fastening material.

It is another object of the present invention to provide a female component for a fastening device that can be used with both commercially available male components having resilient individual hooks, as well as less expensive male components with more brittle hooks than those currently in use.

It is a still further object of the present invention to provide a low cost and improved method for producing a female component for a hook and loop type fastening device.

These and other objects of the present invention will be more readily apparent when considered in reference to the following description and when taken in connection with the accompanying drawings.

SUMMARY OF THE INVENTION

The present invention provides a loop fastening material having an elastomeric adhesive backing and a multiplicity of fibrous elements extending from the backing. The fibrous elements are formed by filaments positioned on the backing when the backing is in an elongated orientation. The filaments are preferably positioned on the backing essentially parallel to each other and essentially parallel or perpendicular to the path of response of the backing material. The filaments are preferably intermittently secured to each other at spaced, fixed regions so that the fixed regions define therebetween catching regions. Thus, the fibrous elements are formed by shirring of the filaments at the catching regions when the backing material is returned to its relaxed orientation.

The loop fastening material is formed by a method comprising the steps of:

(a) providing a first lamina comprising an elastomeric, pressure-sensitive adhesive film having a first adhesive surface and a second adhesive surface opposed to said first adhesive surface, a relaxed orientation and an elongated orientation;

(b) stretching said first lamina from said relaxed orientation to said elongated orientation;

(c) contacting a second lamina comprising a nonwoven web with said first surface of said first lamina in said elongated orientation, thereby directly joining said second lamina and said first lamina to form a laminate; and (d) relaxing said first lamina such that said second lamina is shirred to form catching regions capable of entangling the hooks of a complementary male fastening component.

The present invention also relates to a fastening device having a hook fastening material and a loop fastening material. The loop fastening material comprises the improved loop fastening material of the present invention. The hook fastening material comprises any of the well known hook fastening materials as are known in the art and which have a base and a number of engaging elements extending from the base. The loop fastening material and the complimentary hook fastening material provide a secure closing means that will resist shear stress and peel forces encountered during use.

The present invention also relates to disposable articles and more particularly to a disposable diaper having such an improved fastening device.

DETAILED DESCRIPTION OF THE INVENTION

Overall Characteristics of the Refastenable Fastening Device

Figure 4:
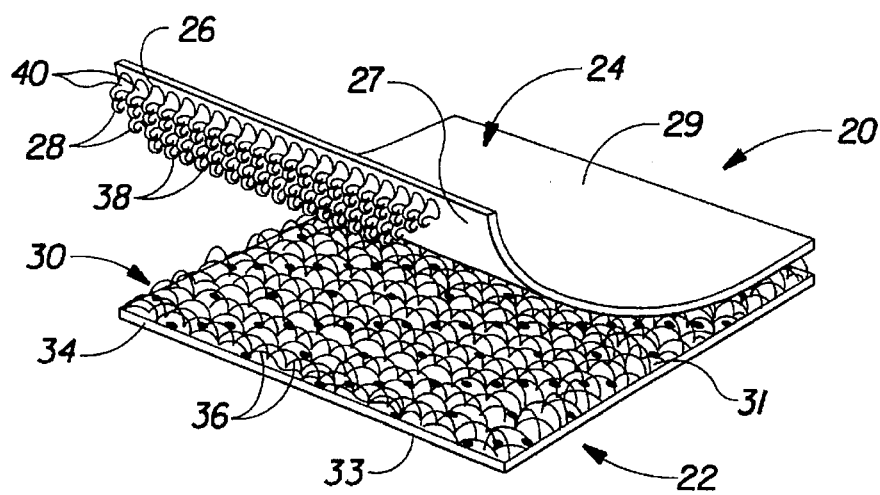
FIG. 4 is a perspective view of a fastening device according to the present invention.

A preferred embodiment of the refastenable fastening device of the present invention, fastening device 20, is shown in FIG. 4. The fastening device 20 comprises a nonwoven female component 22 and a complementary hook fastening component 24.

Figure 1:
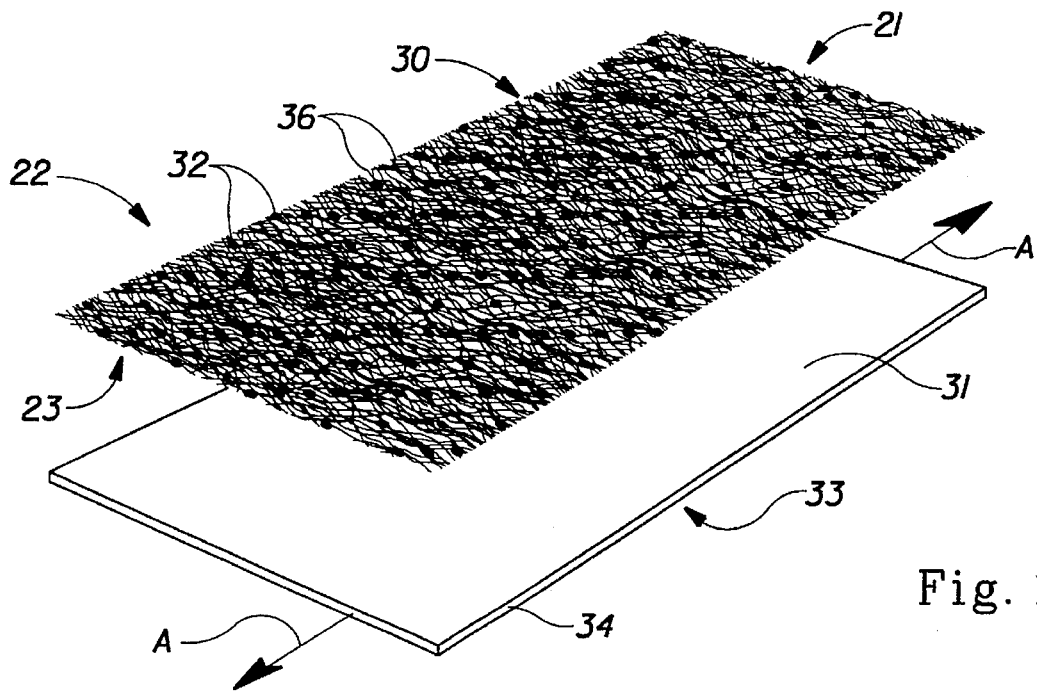
FIG. 1 is a perspective view of the filaments and the backing used to form the present invention prior to the filaments being positioned or laid down on the backing.

The female portion of the device, more specifically, the nonwoven female component (or simply "female component") 22 receives and engages the hooks 28 of the male component. The female component 22 shown in FIGS. 3 and 4 comprises at least one nonwoven web 30 secured to a backing 34. As shown in FIG. 1, the nonwoven web 30 has an outwardly-facing surface 21 and an inwardly-facing surface 23 opposed to the outwardly-facing surface 21. The nonwoven web 30 comprises a plurality of filaments (or fibers) 36 that entangle the hooks 28 of the male component 24. The backing has a first surface 31 and a second surface 33 opposed to the first surface 31, and preferably comprises an elastomeric adhesive.

The male portion of the device, more specifically, the hook fastening component (or simply "hook component") 24, comprises a base 26 having a first surface 27 and a second surface 29. The base 26 comprises a plurality of upstanding engaging elements, or "hooks" 28, extending from the first surface 27. The term "hook" is nonlimiting in the sense that the engaging elements may be in any shape known in the art so long as they are adapted to engage a complimentary loop fastening component or the female component 22 of the present invention. The hooks 28 generally have heads 38 (or engaging means) which are disposed on top of the shanks, or stems 40, that extend from the first surface 27 of the male component 24.

The fastening device 20 of the present invention functions in the following manner. The fastening device 20 is closed when the female component 22 and the male component 24 are pressed face-to-face against each other. When this happens, the hooks 28 are entangled by the fibers 36 of the nonwoven web 30. The nonwoven web 30 provides space for the hooks, particularly, the heads 38 of the hooks to occupy when the fastening device 20 is closed. The backing 34 provides a supporting foundation for the nonwoven web 30. With the hooks 28 mechanically entangled by, or "hooked", onto the fibers 36 (shown in the portion of the fastening device 20 to the right side in FIG. 4), the connection between the components resists the forces that may be exerted on the fastening device 20.

The fastening device 20 is opened by peeling the male component 24 away from the female component 22 (or by peeling the female component 22 away from the male component 24). If the male component 24 has resilient hooks, the peeling action may cause the hooks to be bent so that they are disengaged from entanglement with the fibers 36 of the nonwoven web 30. In other cases (particularly if the hooks 28 are relatively inflexible), the hooks 28 may be separated by breaking the fibers 36 of the female component 22. In either case, the hooks 28 are disengaged and the male component 24 is completely detached from the female component 22. The fastening device 20 is then capable of being refastened in the manner described above.

The Female Fastening Component

The term "nonwoven female component", as used herein refers to a female component for a refastenable fastening device that comprises a nonwoven web joined to a backing. (The nonwoven female component may also be referred to as a loop fastening material or simply, a loop fastener.) The term "nonwoven web" refers to fabrics made of fibers held together by interlocking or inter-fiber bonding which are not woven, knitted, felted, or the like. However, the nonwoven web referred to herein may comprise fibers that are initially substantially unbonded which are subsequently bonded to each other.

FIG. 1 shows the backing 34 and the nonwoven web 30 used to form the female component 22 prior to their association. The backing 34, preferably an elastomeric adhesive, is shown in its elongated orientation (stretched in a direction parallel to the line designated A—A). As used herein, the term "elastomeric" refers to materials that extend in at least one direction when a force is applied and return to approximately their original dimensions after the force is released. The nonwoven web 30, as shown in FIG. 1, preferably comprises a multiplicity of filaments 36 that are joined with each other by inter-fiber bonds 32 prior to being associated with the backing 34. As used herein, the term "joined" encompasses configurations whereby an element is directly secured to another element and configurations whereby an element is indirectly secured to another element by affixing an element to intermediate member(s) which in turn are affixed to another element. The term "inter-fiber bonds" refers to bonds that join one or more filaments to one or more other filaments.

Figure 2:
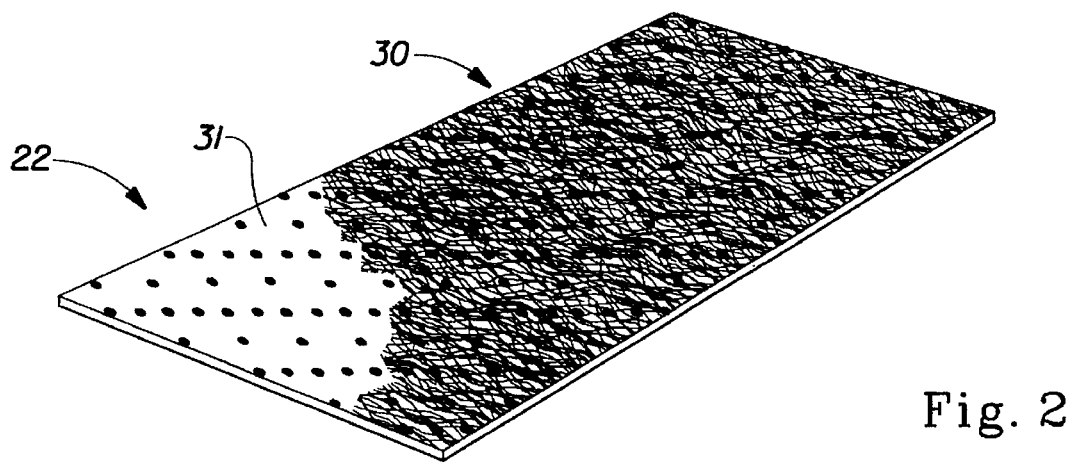
FIG. 2 is a perspective view of the female component of the present invention when the backing is in its elongated orientation.

FIG. 2 shows a preferred embodiment of the female component 22 where the backing 34 is in its elongated orientation after the nonwoven web 30 has been positioned on and joined to the first surface 31 of the backing 34. Preferably, the filaments 36 of the nonwoven web 30 are aligned essentially parallel to each other and essentially perpendicular to the path of response of the backing 34. ("Essentially perpendicular" is used herein to indicate that the filaments 36 need not extend absolutely perpendicular to the path of response so long as the majority of the filaments 36 extend perpendicularly to or a small deviation off perpendicularly to the path of response. As used herein, the term "path of response" refers to the direction in which an elastomeric material in an elongated orientation will respond when the forces acting to elongate the elastomeric material are removed. Further, the filaments 36 of the nonwoven web 30 are preferably in an untensioned state when they are joined to the elongated backing 34.) This helps to ensure that the filaments 36 will become "shirred" when the backing 34 contracts to its relaxed orientation (shown in FIG. 3). The term "shirred" as used herein, refers to the gathering of the filaments 36 of the nonwoven web 30 caused by the contraction of the backing 34 from its elongated orientation to its relaxed orientation such that portions of the filaments 36 that are not secured to the backing 34 or other filaments 36 bend away from the first surface 31 of the backing 34. The shirred filaments 36 form unsecured catching regions 37 (loops) capable of entangling the hooks 28 of a complementary male fastening component 24.

Figure 3:
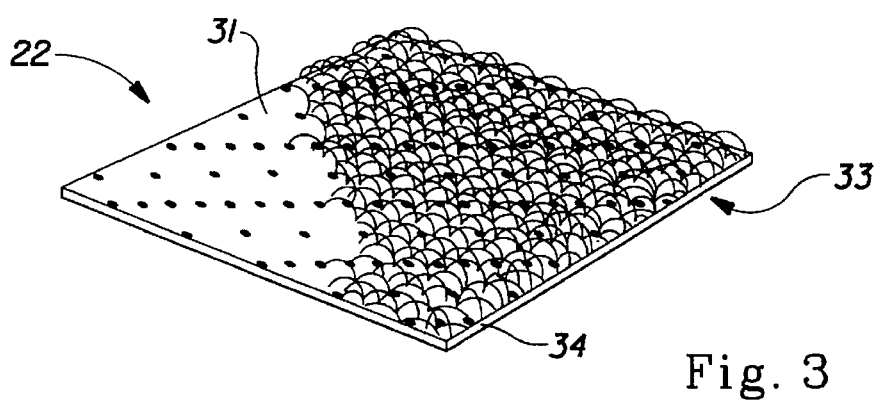
FIG. 3 is a perspective view of the female component of the present invention when the backing is in its relaxed orientation.

FIG. 3 shows a preferred embodiment of the present invention after the nonwoven web 30 and the backing 34 have been joined and after the forces acting to elongate the backing 34 have been removed such that the backing 34 has contracted to its relaxed orientation. The shirred filaments 36 form a multiplicity of fibrous elements 35 extending outwardly from the first surface 31 of the backing 34. Each of the fibrous elements 35 comprises a pair of fixed regions 42 (joined to the backing 34) and an unsecured catching region 37 disposed between the pair of fixed regions 42. The catching regions 37 are capable of securely engaging the hooks of a complementary hook fastening component to provide a fastening device 20, as is shown in FIG. 4.

1. The Nonwoven Web

Figure 5:
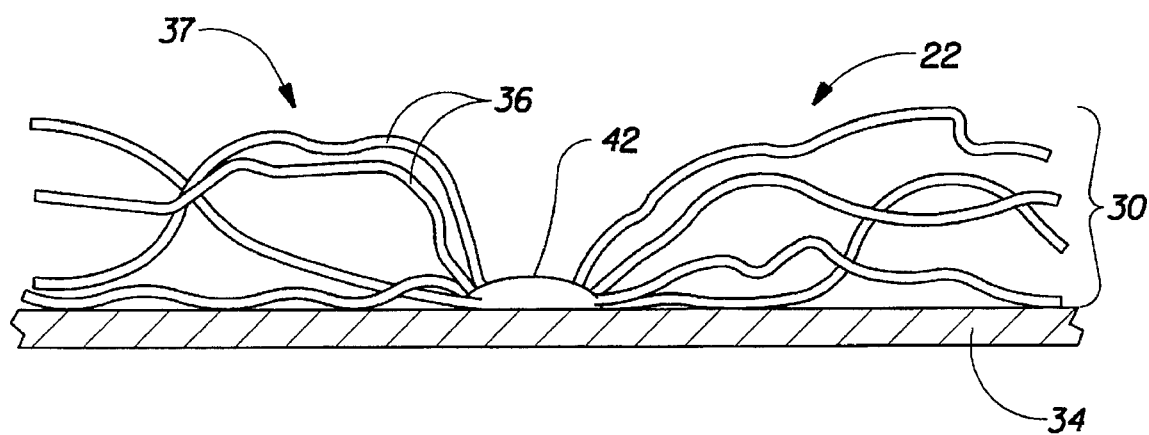
FIG. 5 is a greatly enlarged side view of the fibrous elements of the female component of the present invention.

The fibrous elements 35 of the present invention are preferably formed from filaments 36 positioned on and secured to the backing 34. As used herein, the term "filament" defines a member having a high ratio of length to diameter or width. (FIG. 5 shows a portion of the female fastening component 22 greatly enlarged to show the filaments 36 in detail.) Thus, a filament may be a fiber, a thread, a strand, a yarn or any other member or combination of these members, including filaments that are preattached together in nonwoven webs, as are known in the art. Suitable materials for such filaments 36 include natural fibers such as cotton or wool; synthetic fibers of nylon, polyamides, polyesters, or polyolefins; spun yarns; polyethylene fibers; polypropylene fibers; nylon fibers, non-woven webs; or any other material or combination of materials known in the art and suitable for use herein.

The filaments 36 may be manufactured using a number of manufacturing techniques including those such that the filaments are spun, blown, or the like. Preferably, each filament 36 comprises a polypropylene fibers of between about 2 and about 15 denier. The individual filaments 36 are preferably comprised in a nonwoven web 30 having a basis weight of between about 10 g/yd2 and about 40 g/yd2 (about 12 g/m2 to about 48 g/m2), more preferably between about 15 g/yd2 and about 25 g/yd2 (about 18 g/m2 and about 30 g/m2). The nonwoven web 30 may comprise filaments 36 having similar or different deniers and lengths. Further, the nonwoven web 30 may comprise a mixture of filaments 36 comprising different materials. Some nonwoven webs comprising suitable filaments include the carded polypropylene nonwoven web manufactured by the Veratec Nonwoven Group of the International Paper Company, of Walpole, Mass. under the trade name P-11, the spunbonded polypropylene nonwoven web P-9, and the carded polypropylene nonwoven web P-8. Other suitable nonwoven webs comprising suitable filaments include COROVON spunbonded polypropylene manufactured by Corovin GmbH of Germany, and CELESTRA manufactured by the James River Corporation.

The lengths of the filaments 36 in the nonwoven web 30 depend upon the type of process used to make the nonwoven web 30. For instance, if a carded nonwoven web is used, the filaments 36 that comprise such a web can have lengths that range from about 0.5 inches to about 5 inches (from about 1 cm. to about 13 cm.). In preferred carded nonwoven webs, the filaments are between about 1 inch and about 3 inches (between about 2.5 cm. and about 8 cm.) long. Alternatively, if a spunbonded nonwoven web is used, the filaments 36 of such a web will typically be continuous length. (As used herein, the term "continuous" refers to relatively long filaments that run the entire length of the nonwoven web.)

A preferred filament 36 has a length to make at least one complete fibrous element 35. Thus, for example, the filament 36 may only have a pair of fixed regions 42 positioned adjacent its ends so that the fibrous element 35 is formed of a whole filament 36. More preferably, the filament 36 has a number of fixed regions 42 positioned along its length to form a plurality of fibrous elements 35 along each filament 36. If the filaments 36 are short, or staple, complete fibrous elements 35 having two fixed regions 42 and catching regions 37 may not be formed. The resulting incomplete fibrous elements 35 may not be able to securely engage the hooks 28 of a complementary hook fastening material 24. Thus, the ability of the nonwoven female component 22 to provide a secure closure may be diminished.

The amount of inter-fiber bonding between the filaments 36 of the nonwoven web 30 is also an important factor relevant to the ability of the female component 22 of the present invention to entangle the complementary hook fastening component 24. An excessive number of bond sites created between the filaments 36 in the nonwoven web 30 will tend to interfere with the entry of hooks 28 into the nonwoven web 30, thus reducing the shear strength of the fastening device. (In general, the strength of the fastening device will be increased as more hooks are able to enter and engage the nonwoven web.) Alternatively, too few inter-fiber bonds 32 may increase the number of filaments 36 having loose (unbonded) ends, thus reducing the female component's 22 ability to entangle the hooks 28 of the complementary hook fastening component 24.

In a preferred embodiment of the present invention, the total plan view area of the inter-fiber bonds 32 is between about 1 percent and about 35 percent of the total area of the nonwoven web 30. More particularly, the total plan view area of the inter-fiber bonds is between about 5 percent and about 25 percent of the total area of the nonwoven web. The percentage of inter-fiber bonding is preferably measured by examining a representative sample of the nonwoven web under a microscope. The sample is viewed from directly above the outwardly-facing surface 21 of the nonwoven web 30. The plan view area of each inter-fiber bond 32 is measured. The sum of the areas of the bonds is divided by the area of the sample. The result is the percentage area occupied by the inter-fiber bonds.

The pattern of the inter-fiber bonds within the nonwoven web is another important factor relating to the strength and overall efficacy of the female component. The inter-fiber bonds 32 may be continuous lines or intermittent areas of bonding. Preferably, the inter-fiber bonds 32 are sufficiently close together that the filaments 36 of the nonwoven web 30 have relatively few unbonded loose ends. Thus, the distance between inter-fiber bonds 32 is preferably less than the average length of the filaments 36 in the nonwoven web 30, more preferably, less than about one-half the average length of the filaments 36 in the nonwoven web 30.

In a preferred embodiment of the present invention, the inter-fiber bonds 32 are arranged in a regular pattern. As used herein, the term "regular" refers to bond patterns that are generally similar throughout the area of the nonwoven web 30 when viewed from directly above the outwardly-facing surface 21 of the nonwoven web 30. Suitable inter-fiber bonding patterns include a series of straight or curved lines, or arrangements of inter-fiber bonds 32 that form grids defining different geometrical shapes such as squares, rectangles, hexagons, diamonds, and circles. Such regular patterns will provide the female component 22 with relatively uniform holding characteristics.

One bonding pattern that has been found to work especially well in the female component 22 of the present invention is the intermittent diamond-shaped pattern shown in FIGS. 1 and 2. The "diamonds" in the diamond-shaped pattern comprise a number of intermittent inter-fiber bonds 32 regularly arranged in lines that define the edges of generally square shaped regions. (A preferred arrangement of the inter-fiber bonds 32 of the nonwoven web 30 before the filaments 36 become shirred is shown on the left side of FIG. 2. A preferred arrangement of the inter-fiber bonds 32 of the nonwoven web 30 after the filaments 36 have become shirred is shown on the left side of FIG. 4.). The pattern is rotated approximately 45 degrees to give the appearance of diamonds. Preferably, the dimensions of the pattern should be such that the distance between the inter-fiber bonds 32, in at least some portion of the area between the sides of the diamond-shaped areas, is greater than the projected plan view dimensions of the hooks 28 of the complementary male component 24. (Plan view dimensions of complementary male components are discussed in greater detail below.) Nonlimiting examples of diamond-shaped bonding patterns suitable for use in female component 22 of the present invention include patterns having sides that measure between about ½ inch×½ inch (about 1.3 cm.×1.3 cm.) and about ⅛ in×⅛ in. (about 0.3 cm.×0.3 cm.), more preferably between about ¼ inch×¼ inch (about 0.6 cm.×0.6 cm.) and about ⅜ inch×⅜ inch (about 1 cm.×1 cm.), and most preferably about ¼ inch×¼ inch (about 0.6 cm.×0.6 cm.). A suitable nonwoven web 30 comprising inter-fiber bonds 32 arranged in a diamond-shaped pattern is available from the Veratec Nonwoven Group of the International Paper Company, of Walpole, Mass. under the trade name P-11.

The inter-fiber bonds 32 may be produced by any method that is known in the art. In a preferred embodiment, the inter-fiber bonds 32 are produced by passing a nonwoven web 30 through a pair of rollers that have been heated close to the melting point of the filaments 36 comprised in the nonwoven web 30. One of the rollers preferably has a smooth surface; the complementary roller has a pattern of pins extending from its surface in the diamond-shaped pattern described above. When the nonwoven web 30 passes between the rollers, the heat and pressure of the rollers causes distinct regions of the filaments 36 to melt producing inter-fiber bonds 32 in the preferred diamond-shaped pattern.

The nonwoven web 30 is preferably positioned on and joined with the backing 34 while the backing 34 is in an elongated orientation and while the filaments 36 are in an untensioned condition. While the filaments 36 could conceivably be positioned on the backing 34 in a tensioned or unstable state, such is not preferred to provide maximum shirring of the filaments 36. Further, while the backing 34 could be in a relaxed orientation when the filaments 36 are positioned on the backing 34, this is not preferred because in causing the backing 34 to become elongated, enough filaments 36 may be dislocated, disarranged, skewed or bonded to the backing 34 such that the fibrous elements 35 would not be as effective in engaging the hook fastening component.

The configuration in which the filaments 36 are positioned or laid down on the backing 34 determines the size and the ability of the loop fastening component 22 to provide an effective fastening device. While the filaments 36 may be randomly positioned on the backing 34 such that the filaments 36 overlap or extend in many different directions, it has been found that the filaments 36 should preferably be positioned as parallel with each other as possible to provide fibrous elements 35 configured in a uniform direction. In addition, while the filaments 36 may be positioned lengthwise on the backing 34 in any direction, in order to take advantage of the maximum shirring effect of the backing 34 to form fibrous elements 35 of maximum height, the filaments 36 are preferably positioned on the backing 34 in a direction essentially perpendicular to the path of response of the backing 34. (It has been found, however, that filaments 36 positioned essentially parallel to the path of response also provide suitable entangling ability.) The filaments 36 may be positioned or laid down on the backing 34 by any method or means that is known in the art.

2. The Backing

The backing 34 of the present invention is that part of the female fastening component 22 to which the nonwoven web 30 is secured. The backing 34 is preferably comprised of an elastomeric, pressure sensitive adhesive, so that it may be readily joined to the nonwoven web 30 to form the nonwoven female component 22. As used herein, the term "elastomeric" refers to materials that extend in at least one direction when a force is applied and return to approximately their original dimensions after the force is removed. Thus, elastomeric materials have an elongated orientation (when force is applied) and a relaxed orientation (when force removed). The term "adhesive" refers to materials which are capable of bonding to another material by sticking, or adhering, to the surface of the other material. A "pressure sensitive adhesive" is an adhesive that is responsive to pressure, i.e., is capable of adhering under the influence of pressure alone.

The elastomeric adhesive comprising the backing 34 of the present invention may take on a number of different configurations. For example, the backing 34 may comprise a thin film having a uniform or varying thickness, slits, holes, deformations or the like; a laminate of two or more films; a web of elastomeric adhesive; a single or multiple strands of elastomeric adhesive; discrete regions of elastomeric adhesive formed in random or regular patterns; or any combination of the above. In one preferred embodiment, the backing 34 comprises an elastomeric adhesive that has been extruded in the form of a thin film of about 0.03 mm. to about 1.0 mm. (about 0.001 in. to about 0.04 in.). In a particularly preferred embodiment, the elastomeric film has a thickness of between about 0.025 mm. to about 0.38 mm (about 0.001 in. to about 0.015 in.).

The elastomeric adhesive selected for the backing 34 may comprise any of a number of different elastomeric adhesives as are known in the art. The elastomeric adhesive preferably has an elastic modulus between about 1 and about 30 PSI and more preferably between about 5 and about 15 PSI. (The elastic modulus calculation is preferably determined on the strain interval of about 50% to about 150% elongation of any convenient gage length using the original cross sectional area of the sample prior to straining the sample to determine the elastic modulus.) Further, the elastomeric adhesive should be capable of elongation from about 500 to about 1000 percent in at least one direction without rupture. More preferably, the elastomeric adhesive should be capable of between about 500 percent and about 1000 percent elongation without rupture, not exhibit excessive necking or thinning when elongated, or exhibit excessive hysteresis or delamination upon elongation.

Other characteristics that help define suitable elastomeric adhesives relate to the process in which the present invention is made. As described below, the elastomeric adhesive preferably forms a film that is stretched prior to the application of the nonwoven to the elastomeric adhesive backing. One preferred method of inducing the stretch is to adhere a portion of the elastomeric adhesive film to tentering belts that diverge to stretch the film. The overlap between the film and the tentering belts forms a "lap joint". (The term "diverge" is used herein to mean move apart. The term "lap joint" refers to the area where two overlapping materials are joined together.) Preferably, the tensile strength of the film should be less than the lap shear bond strength between the film and the tentering belts. (As used herein, the term "tensile strength" refers to the pulling stress required to break a given specimen. The term "lap shear bond strength" refers to the force needed to disrupt a lap joint, wherein the force applied is essentially parallel to the surface which adjoins the elastomeric adhesive film and the tentering belts.) Thus, as the tentering belts diverge and stretch the film, the bond between the film and the tentering belts remains in tact.

A pressure sensitive elastomeric adhesive marketed by the Findley Adhesive Corporation of Wauwatosa, Wis. under the trade name 198-338, has been found to be particularly well suited for this purpose. However, other suitable elastomeric materials include H2206 and HS2206, each of which is available from the Findley Adhesive Corporation.

Alternative Embodiments

Figure 6:
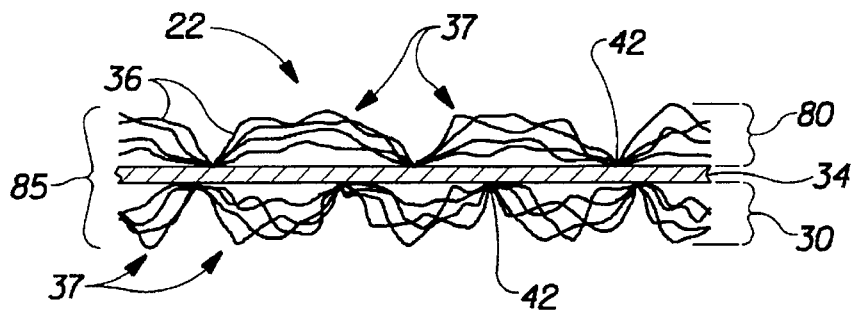
FIG. 6 is a greatly enlarged side view of an alternative tri-laminate embodiment of the present invention.

FIG. 6 shows an alternative embodiment of the female component 22 of the present invention comprising a second lamina 80 joined to the second surface 33 of the elastomeric adhesive backing 34 to form a tri-laminate 85. Joining a second lamina 80 to the elastomeric adhesive backing 34 provides the female fastening component with additional advantages. For instance, the tri-laminate material 85 may be incorporated into a disposable absorbent article, such as a diaper as an elastomeric waistband capable of engaging the hooks of a complementary male fastening component. Further, the tri-laminate 85 provides an elastomeric female fastening component 22 capable of engaging the hooks 28 of a complementary male fastening component 24 on two opposing surfaces.

In an especially preferred alternative embodiment of the present invention, the second lamina 80 comprises a nonwoven web such as the nonwoven web 30 described above with respect to the female fastening component 22. However, a suitable lamina may be manufactured from a wide range of materials, including plastic films; woven webs of natural fibers (e.g. wood or cotton), synthetic fibers (e.g. polyester or polypropylene), or a combination of natural and synthetic fibers; foams; or natural or synthetic rubber.

The second lamina 80 may be joined to the elastomeric adhesive backing 34 in the manner described with respect to the nonwoven web 30 or any other method as is known in the art. Further, the second lamina 80 may be joined to the backing 34 contemporaneously with the nonwoven web 30 when the backing 34 is in an elongated orientation or at any other time after the adhesive backing 34 is formed. In a preferred embodiment, however, the lamina 80 is joined to the backing 34 after the nonwoven web 30 has been joined to the backing 34 and after the backing 34 has been at least partially relaxed. (An elastomeric material in an elongated orientation is "partially relaxed" when the forces stretching the elastomeric material are reduced, allowing the material to contract but not completely relax. Thus, an elastomeric material in a partially relaxed condition is still capable of contracting further to its relaxed orientation after the forces are completely removed.) Joining the second lamina 80 after the backing 34 has been at least partially relaxed ensures that the fibrous elements 35 of the nonwoven web 30 will remain shirred when the female fastening component 22 is stretched. This is because the second lamina 80 will become fully extended to its elastic limit before the nonwoven web 30, thus maintaining at least some shirting in the filaments 36 of the nonwoven web 30. Thus, an elastomeric nonwoven female component 22 is provided that will maintain its ability to entangle the hooks 28 of a complementary male fastening component 24 even after the female component 22 has been stretched to a point where the second lamina 80 is fully extended. (If the second lamina 80 is joined to the backing 34 when the backing 34 is in its fully relaxed orientation, the female component 22 will lose its elastomeric qualities. Thus, such an embodiment is not preferred where the female component must be capable of stretching.)

The Complementary Male Component

The term "male component", as used herein, is used to designate the portion of the fastening device 20 having engaging elements, such as hooks 28. The male components 24 used with the nonwoven female component 22 of the present invention can be conventional, commercially available hook materials. The male component 24, however, is not limited to conventional materials with flexible, resilient hooks 28. Suitable male components can have less expensive, relatively inflexible, more brittle hooks. Further, the engaging elements may have any shape known in the art such as hooks, "T's", mushrooms, or any other shape. One suitable male component 24 may comprise a number of shaped engaging elements projecting from a woven backing such as the commercially available material designated "SCOTCHMATE" brand No. FJ3402 available from Minnesota Mining and Manufacturing Company, St. Paul, Minn. A preferred male component is described in U.S. Pat. No. 4,846,815 entitled "Disposable Diaper Having An Improved Fastening Device" which issued to C. L. Scripps on Jul. 11, 1989. Other particularly preferred male components and methods for making the same are the prongs described in U.S. Pat. No. 5,058,247 entitled "Mechanical Fastening Prong" issued to Thomas et al. on Oct. 22, 1991; U.S. Pat. No. 5,116,563 entitled "Process for Producing a Mechanical Fastener" issued to Thomas et al. on May 26, 1992; U.S. Pat. No. 5,180,534 entitled "Process of Manufacturing A Refastenable Mechanical Fastening System", which issued to Thomas, et al. on Jan. 19, 1993; and U.S. Pat. No. 5,230,851 entitled "Process of Manufacturing a Refastenable Fastening System" issued to Thomas on Jul. 27, 1993. Each of these patents are hereby incorporated by reference herein.

The male component 24 may be manufactured from a wide range of materials. Such suitable materials include, but are not limited to, nylon, polyester, polypropylene, or any combination of these or other materials.

Examples Of Uses Of The Refastenable Fastening Device

The refastenable fastening device of the present invention is especially useful as a fastening device for disposable absorbent articles. The term "disposable absorbent article", as used herein, refers to articles which absorb and contain body exudates. More particularly, the term refers to articles which are placed against or in proximity to the body of the wearer to absorb and contain the various exudates discharged from the body. The term "disposable" means that such articles are intended to be discarded after a single use (i.e., they are not intended to be laundered or otherwise be used). Examples of disposable absorbent articles include diapers, incontinence garments, sanitary napkins, bandages, and the like.

Figures 7, 8:
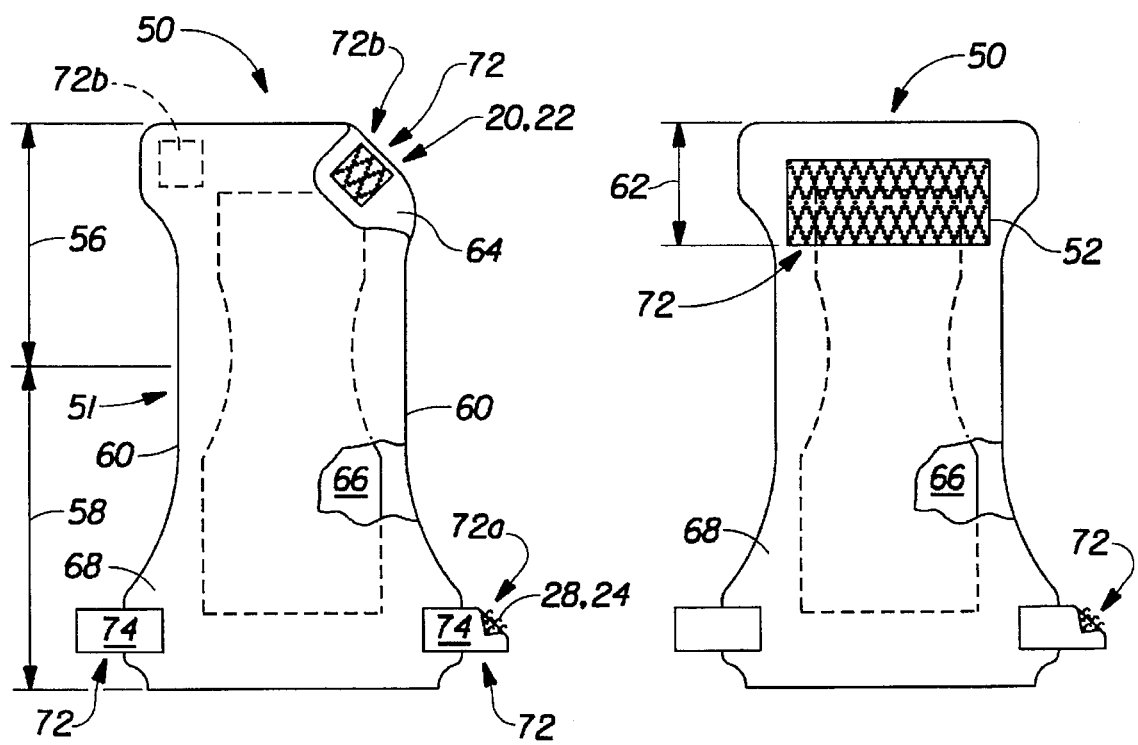
FIG. 7 is a perspective view of a disposable diaper that includes the fastening device of the present invention.
FIG. 8 is a perspective view of a disposable diaper that includes the fastening device of the present invention.

FIGS. 7 and 8 show an exemplary disposable diaper 50 comprising a fastening system 72 including the nonwoven female fastening component 22 of the present invention. The diaper 50 preferably comprises a body portion 51 and two waist regions, a first waist region 56, and a second waist region 58. The body portion 51 preferably comprises a liquid pervious topsheet 64, a liquid impervious backsheet 68, and an absorbent core 66.

As shown in FIG. 7, the fastening system 72 of the diaper 50 comprises the female fastening component 22 of the present invention, among other elements. The fastening system 72 may take on a number of configurations and constructions. In one preferred embodiment, the first fastening element 72a comprises a male component 24. The male component 24 provides hooks 28 that extend from the tab 74 disposed in the second waist region 58. The nonwoven female component 22 of the present invention comprises the second fastening element 72b disposed in the first waist region 56. However, the positions of the components of the fastening device 20 of the present invention could be reversed so that the first fastening element 72a comprises the nonwoven female component 22 and the second fastening element 72b comprises the male component 24.

In an especially preferred embodiment of the disposable diaper 50, the filaments 36 in the nonwoven web 30 of the female component 22 are aligned in a single direction. The female component 22 is oriented so that the filaments 36 in the nonwoven web 30 extend essentially parallel to the longitudinal edges 60 of the diaper 50. This orientation aligns the filaments 36 generally perpendicular to the direction of shear forces applied to the fastening device 20 during use. In this configuration the filaments 36 provide the maximum peel and shear force resistance.

Several examples of well known diaper configurations to which the present invention can be readily adapted are described in U.S. Pat. Nos. 5,151,092 and 5,221,274 both entitled "Absorbent Article With Dynamic Elastic Waist Feature Having A Predisposed Flexural Hinge", issued to Kenneth B. Buell, et al. on Sep. 29, 1992 and Jun. 22, 1993, respectively; co-pending U.S. patent application Ser. No. 08/155,048 entitled "Absorbent Article With Multi-Directional Extensible Side Panels", filed Nov. 19, 1993; and co-pending U.S. patent application Ser. No. 08/203,456 entitled "Absorbent Article With Multiple Zone Structural Elastic-Like Film Web Extensible Waist Feature" filed on Feb. 28, 1994. Each of the above mentioned patents and co-pending patent applications are hereby incorporated by reference herein. It should be understood, however, that the fastening device of the present invention is not limited to use with any specific diaper structure or configuration.

The female fastening component 22 of the present invention may also be used to provide an inexpensive waistband, or any other elastomeric element (or a portion thereof) of an absorbent article, capable of engaging the hooks 28 of a complementary male fastening component 24. (As used herein, the term "waistband" refers to that portion of an absorbent article that partially or wholly encircles the waist of the wearer.) FIG. 8 shows a diaper 50 having a waistband 62 comprising the female fastening component 22 of the present invention. Further examples of diapers suitable for use with the present invention are described in U.S. Pat. No. 4,699,622 entitled "Disposable Diaper Having An Improved Side Closure" which issued to J. W. Toussant, et al. on Oct. 13, 1987; U.S. Pat. No. 5,019,065 entitled "Disposable Absorbent Article With Combination Mechanical and Adhesive Tape Fastener System", issued to Scripps on May 28, 1991; and U.S. Pat. No. 5,242,436 entitled "Absorbent Article With Fastening System Providing Dynamic Elasticized Waistband Fit", issued to Weil et al., on Sep. 7, 1993; each of which is hereby incorporated by reference herein.

Method of Making the Female Fastening Component

The female fastening component 22 of the present invention is made by contacting a nonwoven web comprising inter-fiber bonds with an elastomeric, pressure sensitive adhesive film. The adhesive film is formed and elongated in at least the cross machine direction before it is brought in contact with the nonwoven web. When the adhesive film and the nonwoven web are brought into contact with each other, they are joined to form a laminate comprising the nonwoven web and an elastomeric adhesive backing. The laminate is then contracted such that regions of the nonwoven web become shirred and thus capable of entangling the hooks of a complementary male fastening component.

The following is a detailed description of the process for making the female fastening component 22 of the present invention. Although the description refers to the elastomeric adhesive backing as an "adhesive film", this terminology should not be construed to limit the scope of the invention. As mentioned above, the adhesive backing 34 may take on a number of different configurations including films, laminates, webs, strands, or the like.

Figure 9:
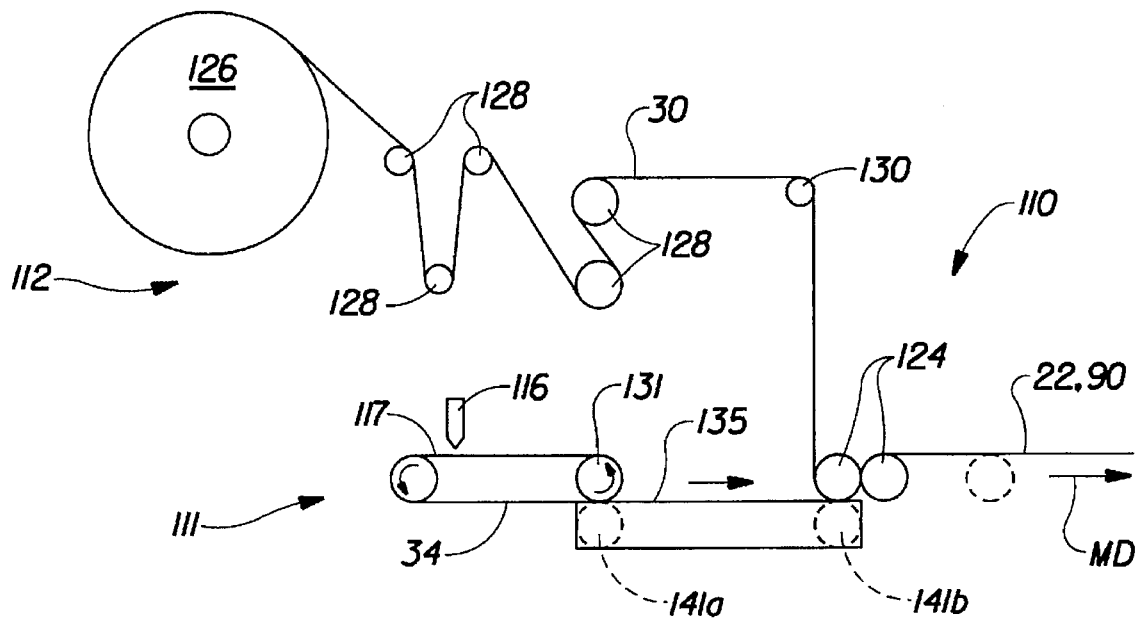
FIG. 9 is a schematic side view of a process for making the female component of the present invention.

The female component 22 of the present invention may be produced on the illustrated apparatus 110, as shown in FIG. 9. The apparatus 110 comprises two separate process modules, process module 111 for the elastomeric adhesive backing 34 (or "adhesive film"), and process module 112 for the nonwoven web 30. The process module 111 comprises an extrusion head 116 and a release surface upon which the extruded adhesive is formed, such as the forming belt 117, to form the elastomeric adhesive backing film 34. (In an alternative embodiment, the elastomeric adhesive backing could be pre-formed and supplied to the line from a roll. This would eliminate the extrusion head 116 and the forming belt 117.)

Examining process module 111 in greater detail, the extrusion head 116 has a slot through which the molten elastic adhesive of the adhesive film 34 is extruded to form a thin film of about 0.03 to about 1.0 millimeters (about 0.001 in. to about 0.04 in.) in thickness, and of any desired width, onto the forming belt 117. An adhesive film 34 having a thickness of about 0.025 to about 0.38 millimeters (0.001–0.015 inches) is particularly preferred. Generally a thicker adhesive film 34 is preferred as the thickness and stiffness of the nonwoven web 30 increases. It will be apparent to one skilled in the art that increasing the thickness of the adhesive film 34 will generally provide a proportional increase in the ultimate strength of the female fastening component 22. An adhesive film 34 of about 8.4 g/cm2 has been found to be suitable.

The extrusion head 116 extrudes the molten adhesive onto the forming belt 117 which cools the molten adhesive into an adhesive film 34 suitable for processing and transports the adhesive film 34 to the tentering belts 135. A roll may be utilized in conjunction with the belt 117 to provide additional cooling and a nip for compression of the adhesive film 34. Further, the adhesive film 34 may be separated from the forming belt 117 by a doctor blade (not shown).

After being removed from the forming belt 117, the application roll 131 guides spaced apart regions of the adhesive film 34 onto the surface of the tentering belts 135. (As used herein, the term "spaced apart" refers to regions of the adhesive film 34 that are spaced apart in the cross machine direction form each other.) The adhesive nature of the adhesive film 34 permits the adhesive film 34 to be secured to the tentering belts 135 without any additional securement means, as are generally used in the art. Preferably, only about ¼ inch to about ¾ inch of the edges of the adhesive film 34 should be secured to the working surface of each tentering belt 135. (It should be noted, however, that the tentering belts could be designed such that a vacuum assists in holding the film in contact with the tentering belts.) The spaced apart regions of the adhesive film 34 are adhered to the working surfaces of the tentering belts 135 forming continuous lap joints. (As used herein, the term "continuous" means relatively unbroken or without interruption.) The continuous nature of the lap joint helps to ensure that the adhesive film 34 will be more evenly stretched than films that are elongated by stretching means comprising discrete mechanical clamping devices.

The tentering belts 135 are spaced apart in the cross machine direction and diverge as they move in the machine direction. The tentering belts 135 preferably comprise a substantially flat working surface to which the adhesive film 34 is adhered, and members that help provide positive control of the belts in both the machine and the cross machine directions. The working surface of each tentering belt 135 is preferably comprised of any material, such as TEFLON, to which the adhesive film 34 will adhere sufficiently in shear to stretch the adhesive film 34, and from which the adhesive film 34 can peeled off without damaging the adhesive film 34 when it is removed. One belt with a suitable working surface is available from F. M. Sheppard & Co. of Erlanger, Ky., and is sold as Belt Style No. 3W11-2A.

Figure 13:
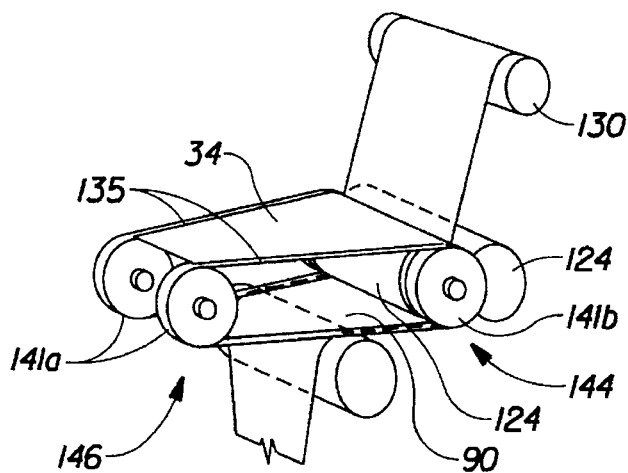
FIG. 13 is an isometric view of a part of the process for making the female component of the present invention.

Each tentering belt 135 travels about a pair of pulleys. As shown in FIG. 13, belts 140 and 142 travel about pulleys 141a and 142b. Pulley 141a defines the converging end 146 of the belts 140 and 142 while pulley 141b defines the diverging end 144 of the belts. In one preferred embodiment, the pulleys 141a and 141b comprise V shaped grooves and the tentering belts 140 and 142 comprise V shaped extensions that ride in the complementary V shaped grooves of the pulleys 141a and 141b, to provide machine direction control of the belt in the cross machine direction.

The tentering belts 135 may be driven by any driving means well known in the art and are preferably not driven by the adhesive film 34. In one preferred embodiment, each tentering belt 135 comprises teeth and grooves that coact with the complementary driving means to provide cross machine directional control of the belt as it is driven forwardly.

Figure 10:
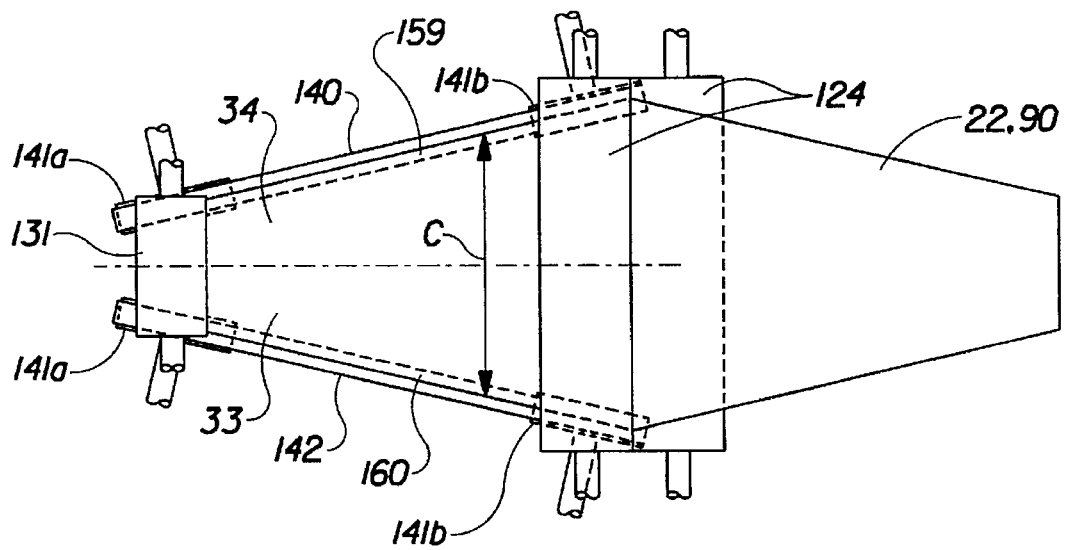
FIG. 10 is a schematic top view of a part of the process for making the female component of the present invention.

One embodiment of the present invention, as shown in FIG. 10, comprises two tentering belts 135, a first belt 140 and a second belt 142. A first region 159 of the second surface 33 of the adhesive film 34 is adhered to the first belt 140, and a second region 160 of the second surface 33 of the adhesive film 34 is adhered to the second belt 142. The first belt 140 and the second belt 142 diverge as they move in the machine direction, stretching the adhesive film 34 in the cross machine direction. (The cross machine direction is denoted by the arrow C in FIG. 10.) This configuration is preferred when it is desired that the adhesive film 34 be evenly stretched. (Alternative embodiments comprising more than two tentering belts are discussed below.)

As shown in FIG. 9, the nonwoven web 30 is taken from the unwind roll 126 and preferably passes through the S-wrap tensioning roll 128 to provide for proper tensioning and to prevent puckering or bunching of the nonwoven web 30. Guide roll 130 guides the nonwoven web 30 into the nip between the combining rolls 124. If necessary, a tracking system (not shown) as is commonly utilized and known in the art, may be employed in the process module 112 to optimally track and adjust the webs of nonwoven web 30 into the nip between the combining rolls 124. A tracking system manufactured by the Fife Corporation of Oklahoma City, Okla., and sold as Model Op6 LRA may be suitable.

The nip between the combining rolls 124 compresses the nonwoven web 30 into superposing contacting relationship with the elastomeric adhesive backing 34, causing the pressure sensitive adhesive backing 34 to bond to the nonwoven web 30, joining the two materials to form the female fastening component 22. As used herein, the term "superpose" or "superposing" will refer to one layer of material having a particular geometric shape being laid upon another layer of material having a substantially similar geometric shape such that all like parts of the two layers of material substantially coincide.

The combining rolls 124 may take on any number of different configurations, as are known in the art. For example, the combining rolls 124 may have smooth surfaces or may have grooves, teeth or any patterns of indentations and/or raised areas on their surfaces. Further, the combining rolls 124 may be identical or may have different surface characteristics, as described above.

Once the nonwoven web 30 and the elastomeric adhesive backing 34 have been joined to form the female fastening component 22, the laminate 90 is returned to a relaxed condition. In this configuration, the nonwoven web 30 will become gathered in at least the direction parallel to the path of response of the adhesive film 34, which will form ridges, wrinkles, or furrows extending outwardly from the first surface 31 of the female component 22 capable of entangling the hooks 28 of a complementary male fastening component 24. The elastomeric laminate 90 will be elastically extensible in the direction parallel to the path of response of the adhesive film 34 up to about the free length of the nonwoven web 30.

Figure 11:
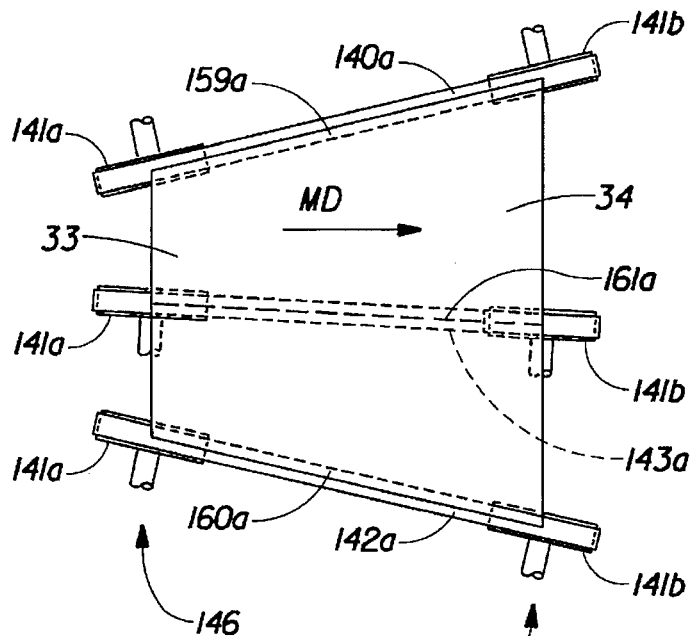
FIG. 11 is a schematic top view of an alternative embodiment of the process for making the female component of the present invention.

Contracting the laminate 90 to a relaxed condition can be accomplished in a number of ways, including simply removing the laminate 90 from the tentering belts 135 and allowing it to contract. More preferably, however, as shown in FIG. 13, the laminate 90 can remain adhered to the belts 140 and 142 as they travel from the diverging end 144 towards the converging end 146 of their cycle. As the belts 140 and 142 travel from the diverging end 144 toward the converging end 146, the belts 140 and 142 converge, and thus contract the laminate 90. (As used herein, the terms "converge" and "converging" mean to move closer together.) Alternatively, as shown in FIG. 11, the laminate 90 may be removed from the belts 140 and 142 and transported to a separate configuration of converging belts 158. Although the converging belts 158 may take on a number of different configurations, a detailed description of one preferred embodiment of the converging belts is described in the co-pending U.S. application Ser. No. 08/254,812, entitled "Apparatus For Continuously Stretching or Continuously Releasing Stretching Forces From A Web Using Two Pairs of Opposing Non-Planar Belts", filed on Jun. 6, 1994, in the names of L. John Viltro, et al. which is incorporated herein by reference.

After the laminate 90 is contracted, it is removed from either the tentering belts 135 or the converging belts 158, leaving exposed the pressure sensitive adhesive of the second surface 33 of the adhesive backing 34. The exposed surface may be used to bond the female fastening component 22 to an absorbent article or any other desired article, or may be deactivated by blocking as is commonly known in the art so that the adhesive of the elastomeric adhesive backing 34 does not bond to other materials through the pressure sensitive properties of the elastomeric adhesive backing 34. Blocking is accomplished by an adhesive deactivation system (not shown) applying a powder of resin to the exposed face of the elastomeric adhesive backing 34. Suitable resin powders include talcum powder, polyolefinic powders, and preferably a resin similar to that used for the nonwoven web 30. Alternatively, the exposed face of the elastomeric adhesive backing 34 may be deactivated by applying a non-adhesive elastomeric film, nonwoven, foam or any other suitable non-adhesive material thereto. An example of one suitable non-adhesive elastomeric film is H2901 manufactured by Findley Adhesives Corporation of Wauwatosa, Wis.

Alternative Embodiments

One preferred alternative embodiment of the present invention for providing regions of differential stretch throughout the adhesive film 34, as shown in FIG. 11, comprises three tentering belts, a first belt 140a, a second belt 142a, and a third belt 143a. (As used herein, the term "differential stretch" refers to areas of the adhesive film 34 that have been unequally elongated.) As discussed above, spaced apart regions of the second surface 33 of the adhesive 34 are adhered to each of the tentering belts. In this particular embodiment, a first region 159a of the adhesive film 34 is adhered to the first belt 140a, a second region 160a of the adhesive film 34 is adhered to the second belt 142a and a third region 161a of the adhesive film is adhered to the third belt 143a. As the belts move in the machine direction, the first belt 140a and the second belt 142a diverge at a rate different from the rate at which the second belt 142a and the third belt 143a diverge, thus producing two regions of differential stretch in the adhesive film 34.

Figure 12:
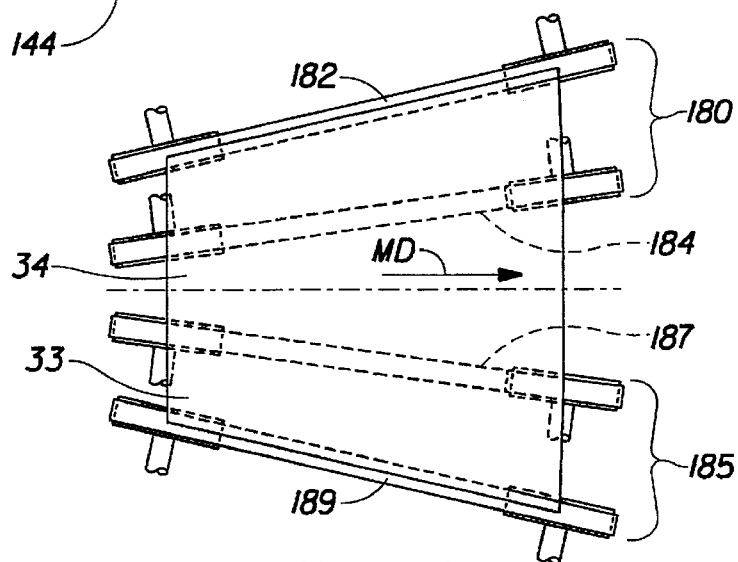
FIG. 12 is a schematic top view of an alternative embodiment of the process for making the female component of the present invention.

Another preferred alternative embodiment, as shown in FIG. 12, comprises a first pair 180 of tentering belts comprises belts 182 and 184, and a second pair 185 of tentering belts comprises belts 187 and 189. Each of said belts contacts a different spaced apart region of the second surface 33 of the adhesive film 34. As the pairs of belts move in the machine direction, they diverge at different rates producing areas of differential stretch throughout the adhesive film 34. (Of course, the first pair 180 could comprise tentering belts 184 and 187 and the second pair 185 could comprise the tentering belts 182 and 189.) Further, numerous other configurations are contemplated wherein some of the tentering belts diverge and others run parallel to each other, thus producing an adhesive film 34 having portions that are stretched between the diverging belts and other portions that are left unstretched between the parallel belts. (Although some preferred embodiments have been discussed, it should be noted that any number of tentering belts may be used to produce any combination of stretched and relaxed regions throughout the adhesive film 34.)

Yet another alternative embodiment of the present invention provides a female fastening component 22 with multi-directional stretch. In this embodiment, the adhesive film 34 may be drawn through the nip formed between a pair of tensioning rolls (not shown). The tensioning rolls provide for machine direction stretching the adhesive film 34 prior to being applied to the tentering belts 135, this provides a laminate which is elastically extensible in two directions, i.e., the machine direction and the cross machine direction. A laminate which is elastically extensible in the machine direction and methods of forming such a laminate are described in greater detail in U.S. Pat. No. 5,032,120, entitled "Disposable Absorbent Article Having Improved Leg Cuffs", issued Jul. 16, 1991, to Mary E. Freeland and Patrick J. Allen, which is incorporated herein by reference.

Method of Making a Tri-laminate Embodiment

Figure 14:
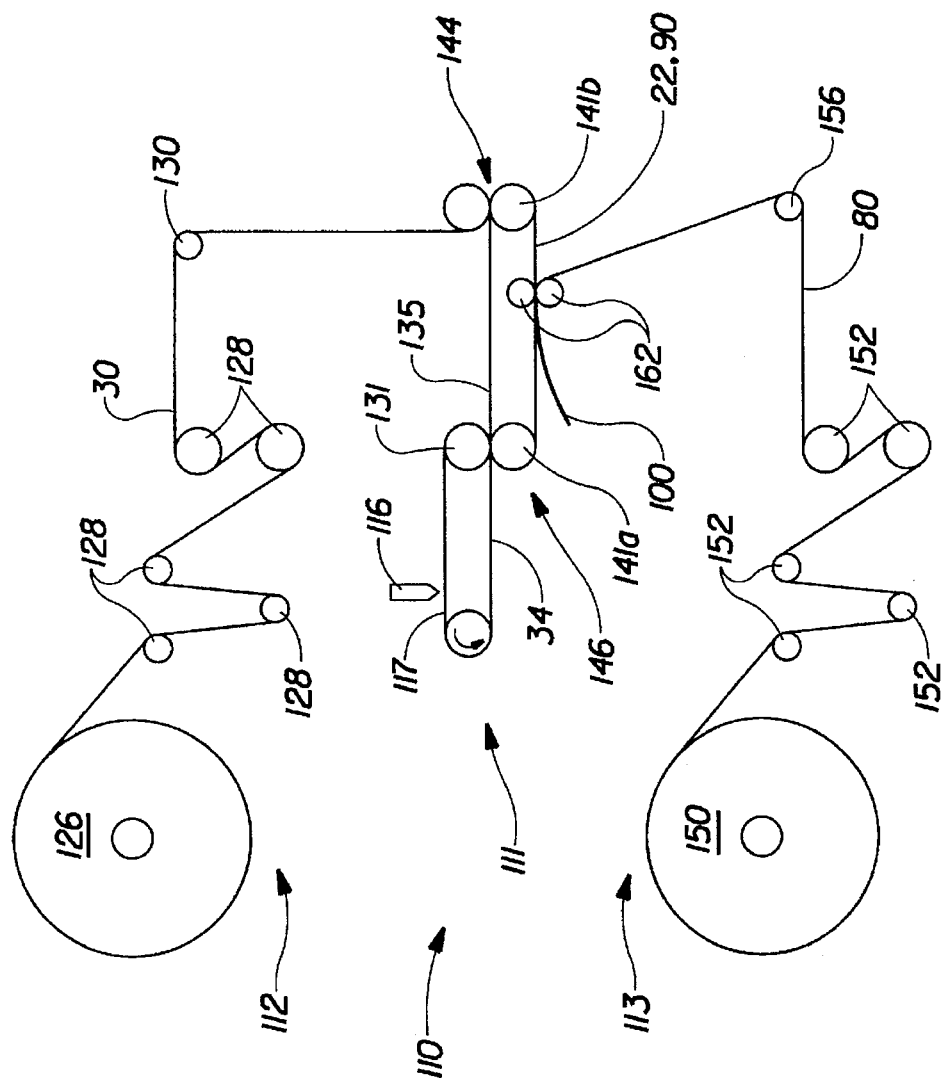
FIG. 14 is a schematic side view of one embodiment of the process for making the tri-laminate embodiment of the present invention.
Figure 15:
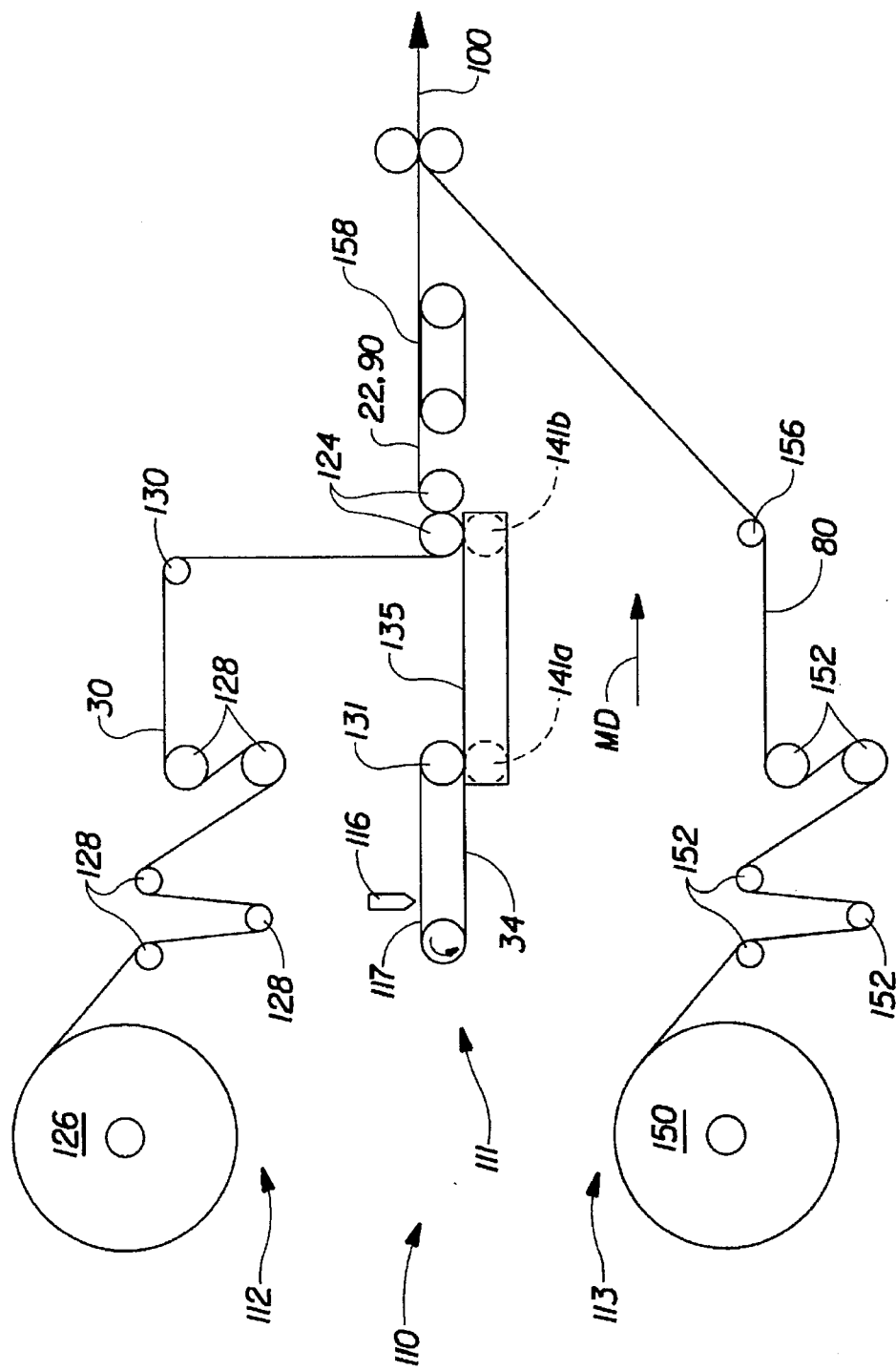
FIG. 15 is a schematic side view of an alternative embodiment of the process for making the tri-laminate embodiment of the present invention.

The above-described method of producing a female fastening component comprising a single nonwoven web 30 joined to the first surface 31 of the elastomeric adhesive film 34 can also be used to produce a tri-laminate female fastening component comprising a nonwoven web 30, joined to the first surface 31 of the backing 34 and a second lamina 80 joined to the second surface 33 of the backing 34. As described above, the nonwoven web 30 and the backing 34 are joined to form the laminate 90. However, when the laminate 90 exits the nip between combining rolls 124, the exposed face of the adhesive backing 34 is not deactivated as described above. Rather, as shown in FIG. 14, the laminate 90 is allowed to remain on the tentering belts 135 as the tentering belts 135 move from the diverging end 144 of their cycle toward the converging end 146 of their cycle. Alternatively, as is shown in FIG. 15, the laminate 90 may be transported to the separate converging belts 158. In either case, the laminate 90 may be partially or fully relaxed prior to application of a second lamina 80.

The second lamina 80 is provided by the additional process module 113, as is shown in FIGS. 14 and 15. The second lamina 80 is taken from the unwind roll 150 and preferably passes through the S-wrap tensioning roll 152 to provide for proper tensioning and prevent puckering or bunching of the lamina 80. Guide roll 156 guides the second lamina 80 into the combining rolls 162. If necessary, a tracking system, not shown, as is commonly utilized and known in the art, may be employed in the process module 113 to optimally track and adjust the second lamina 80 into the combining rolls 162.

After the laminate 90 comprising the nonwoven 30 and the elastomeric adhesive backing 34 exits the converging belts 158, the second surface 33 of the adhesive backing 34 is brought into contact with the second lamina 80. The laminate 90 and the second lamina 80 are passed through the nip of combining rolls 162 under sufficient pressure for the adhesive 34 to adhere to the lamina 80, thus forming the tri-laminate female fastening component 100.

In a preferred embodiment, the second lamina 80 is joined to the adhesive backing 34 after the laminate 90 has been at least partially, yet not fully relaxed. (This creates a tri-laminate with the characteristics and benefits described above with respect to one alternative embodiment of the present invention as shown in FIG. 6.) Preferably, the second lamina 80 is joined to the adhesive backing 34 after the laminate 90 has been relaxed such that the lateral dimensions of the laminate 90, after converging, is between about 90% and about 50% of the lateral dimensions of the lamina 22 when fully stretched. In an especially preferred embodiment, the second lamina 80 is joined to the adhesive backing 34 after the laminate 90 has been relaxed such that the lateral dimensions of the laminate 90, after converging, is about 70% of the lateral dimensions of the laminate 90 when fully stretched. However, embodiments are contemplated wherein the second lamina 80 is joined after the laminate 90 is completely relaxed, or while the laminate 90 is fully stretched.

After the tri-laminate 100 has been formed, as described above, the tri-laminate 100 may be adhered to an absorbent article or any other desired object. The process of forming the tri-laminate 100 leaves exposed the portions of the second surface 33 that were adhered to the tentering belts 35. Thus, the portions of the second surface 33 of the adhesive film that were adhered to the tentering belts 35 can be used to join the tri-laminate 100 to any desired object without the use of any additional adhesive.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A female component of a refastenable fastening device capable of engaging a complementary hook fastening component, said female component comprising:

an elastomeric adhesive backing having an elongated orientation, a relaxed orientation, and a path of response along which said material contracts from said elongated orientation to said relaxed orientation; and a nonwoven web in contact with, and thereby secured to, said elastomeric adhesive backing, said nonwoven web being secured to said elastomeric adhesive backing while said backing is in said elongated orientation, said nonwoven web comprising a multiplicity of fibrous elements comprising filaments that are joined together with inter-fiber bonds at spaced, fixed regions along the length of each of said filaments to define between each pair of fixed regions an unsecured catching region, wherein said fibrous elements comprise those filaments that are shirred when said backing contracts to said relaxed orientation.

2. The female fastening component of claim 1 wherein said filaments are positioned on said backing essentially perpendicular to said path of response of said elastomeric adhesive backing.

3. The female fastening component of claim 1 wherein said filaments are randomly positioned on said elastomeric adhesive backing.

4. The female fastening component of claim 1 wherein said nonwoven web comprises carded polypropylene filaments.

5. The female fastening component of claim 1 wherein said inter-fiber bonds are arranged in a diamond-shaped pattern.

6. A disposable absorbent article comprising a liquid pervious topsheet, a liquid impervious backsheet joined with said topsheet, an absorbent core positioned between said topsheet and said backsheet, and a fastening system for fastening said disposable absorbent article about a wearer, wherein said fastening system comprises the female fastening component of claim 1.

7. The disposable absorbent article of claim 6 further comprising a waistband, wherein said waistband comprises said female fastening component.

* * * * *